(12) United States Patent
Schaub et al.

(10) Patent No.: US 8,703,994 B2
(45) Date of Patent: Apr. 22, 2014

(54) PROCESS FOR PREPARING FORMAMIDES AND FORMIC ESTERS

(75) Inventors: Thomas Schaub, Neustadt (DE); Rocco Paciello, Bad Dürkheim (DE); Marek Pazicky, Heidelberg (DE); Giuseppe Fachinetti, Pisa (IT); Debora Preti, Nodica-Vecchiano (IT)

(73) Assignee: BASF SE (DE)

( * ) Notice: Subject to any disclaimer, the term of this patent is extended or adjusted under 35 U.S.C. 154(b) by 0 days.

(21) Appl. No.: 13/559,011

(22) Filed: Jul. 26, 2012

(65) Prior Publication Data

US 2013/0102807 A1    Apr. 25, 2013

Related U.S. Application Data

(60) Provisional application No. 61/512,020, filed on Jul. 27, 2011.

(51) Int. Cl.
*C07C 69/02* (2006.01)
*C07C 67/00* (2006.01)
*C07C 233/00* (2006.01)

(52) U.S. Cl.
USPC ............................ 560/231; 560/239; 564/215

(58) Field of Classification Search
None
See application file for complete search history.

(56) References Cited

U.S. PATENT DOCUMENTS

2013/0006015 A1*  1/2013  Fachinetti et al. ............ 562/609

FOREIGN PATENT DOCUMENTS

| WO | WO-2012/000799 A1 | 1/2012 |
|---|---|---|
| WO | WO-2012/000823 A1 | 1/2012 |
| WO | WO-2012/000964 A1 | 1/2012 |
| WO | WO-2012/034991 A1 | 3/2012 |
| WO | WO-2012/084691 A1 | 6/2012 |

OTHER PUBLICATIONS

U.S. Appl. No. 61/316,841, filed Mar. 24, 2010, BASF SE.
U.S. Appl. No. 61/392,062, filed Oct. 12, 2010, BASF SE.
U.S. Appl. No. 61/505,186.
U.S. Appl. No. 61/512,023.
U.S. Appl. No. 61/494,896.
Arpe, H.-J., Industrielle Organische Chemie, 6th ed. (2007), pp. 48-49.

(Continued)

*Primary Examiner* — Karl J Puttlitz
(74) *Attorney, Agent, or Firm* — Novak Druce Connolly Bove + Quigg LLP

(57) ABSTRACT

A process for preparing carboxylic acid derivatives of the formula H—(C=O)—R,
R is $OR^1$ or $NR^2R^3$, $R^1$ is optionally substituted $C_1$-$C_{15}$-alkyl, $C_5$-$C_{10}$-cycloalkyl, $C_5$-$C_{10}$-heterocyclyl, $C_5$-$C_{10}$-aryl or $C_5$-$C_{10}$-heteroaryl, substituents are $C_1$-$C_{15}$-alkyl, $C_1$-$C_6$-alkoxy, $C_5$-$C_{10}$-cycloalkyl or $C_5$-$C_{10}$-aryl; $R^2$ and $R^3$ are independently hydrogen or optionally substituted $C_1$-$C_{15}$-alkyl, $C_5$-$C_{10}$ cycloalkyl, $C_5$-$C_{10}$-heterocyclyl, $C_5$-$C_{10}$-aryl or $C_5$-$C_{10}$-heteroaryl, substituents are selected from the group consisting of $C_1$-$C_{15}$-alkyl, $C_5$-$C_{10}$-cycloalkyl and $C_5$-$C_{10}$-aryl or
$R^2$ and $R^3$ together with the nitrogen atom form a five- or six-membered ring which optionally comprises one or more heteroatoms selected from O, S and N and bearing the substituent $R^4$,
$R^4$ is hydrogen or $C_1$-$C_6$-alkyl; by reacting a reaction mixture comprising carbon dioxide, hydrogen and an alcohol of the formula $R^1$—OH or an amine of the formula $NHR^2R^3$ in the presence of a catalyst comprising gold at a pressure from 0.2 to 30 MPa and a temperature from 20 to 200° C. in a hydrogenation reactor.

13 Claims, 1 Drawing Sheet

(56) References Cited

OTHER PUBLICATIONS

Leitner, W., "Carbon Dioxide as a Raw Material: The Synthesis of Formic Acid and Its Derivatives from CO2", Angew. Chem. Int. Ed. Engl., (1995), pp. 2207-2221.

Applied Homogeneous Catalysis with Organometallic Compounds, vol. 2, Cornils and Herrmann eds., (1996), pp. 1058-1072.

Kayaki, Y., et al., "Amphiphilic Resin-Supported Ruthenium (II) Complexes as Recyclable Catalysts for the Hydrogenation of Supercritical Carbon Dioxide", Adv. Synth. Catal., vol. 345, (2003), pp. 175-179.

Liu, J., et al., "Synthesis of Dimethylformamide from CO2, H2 and Dimethylamine over Cu/ZnO", Chem. Commun., vol. 46, (2010, pp. 5770-5772.

Henkel, K. D., et al, "Reator Types and Their Industrial Applications" and in Ullmann's Encyclopedia of Industrial Chemistry, (2005), Wiley-VCH Verlag GmbH & Co. KGaA, DOI: 10.1002/14356007.b04_087.

\* cited by examiner

US 8,703,994 B2

PROCESS FOR PREPARING FORMAMIDES AND FORMIC ESTERS

CROSS-REFERENCE TO RELATED APPLICATIONS

This application claims benefit of provisional application Ser. No. 61/512,020 filed Jul. 27, 2011, which is incorporated herein by reference.

BACKGROUND OF THE INVENTION

The present invention relates to a process for preparing formamides and formic esters, i.e. formamide and its N-substituted derivatives and also esters of formic acid and alcohols, starting from carbon dioxide and hydrogen.

Formamide and its N-substituted derivatives are important selective solvents and extractants because of their polarity. They are used, for example, for the extraction of butadiene from $C_4$ fractions, of acetylene from $C_2$ cracking fractions and of aromatics from aliphatics.

Formic esters such as methyl formate or ethyl formate are used as foaming agents or fragrances.

All industrial production processes for preparing formamide and its alkyl derivatives and also formic esters have hitherto utilized carbon monoxide as $C_1$ building block.

Formamide, N-alkylformamides and N,N-dialkylformamides are prepared by reacting methyl formate, which can be obtained by reaction of carbon monoxide with methanol, with ammonia, N-alkylamines and N,N-dialkylamines, respectively. The methanol liberated here can be recirculated to the synthesis of methyl formate from carbon monoxide and methanol. Other formic esters are obtained by reacting formic acid with the corresponding alcohol with elimination of water.

In a further synthesis which is likewise used in industry, ammonia or the abovementioned amines are reacted at from 20 to 100° C. and from 2 to 10 MPa directly with carbon monoxide instead of methyl formate. The reaction is carried out in methanol as solvent using alkoxides as catalysts (Hans-Jürgen Arpe, Industrielle Organische Chemie, 6th edition, 2007, pages 48 to 49).

Carbon monoxide is a comparatively expensive $C_1$ building block. A further disadvantage of carbon monoxide is its toxicity, which makes it necessary to work with strict safety precautions. Furthermore, the relatively high pressures in the preparation of formamides from carbon monoxide are costly.

Numerous attempts have therefore been made to replace carbon monoxide by the cheap, nontoxic $C_1$ building block carbon dioxide which is available in large quantities (e.g. Applied Homogeneous Catalysis with Organometallic Compounds, volume 2, pages 1058 to 1072, 1996, VCH Verlagsgesellschaft and W. Leitner, Angew. Chem. Int. Ed. Engl. 1995, 34, pages 2207 to 2221). However, most of these studies use homogeneously dissolved catalysts which are difficult to separate off from the product and recirculate to the hydrogenation.

Attempts have been made to immobilize the homogeneous catalysts on support materials so that they can be separated off more easily. This process has been described for dimethylformamide in Y. Kayaki, Y. Shimokawatoko, T. Ikariya, Adv. Synth. Catal. 2003, 345, 175-179. However, this concept requires specific support materials which are complicated to produce, e.g. diphosphine-modified polystyrenes or silica gels. Another disadvantage is that the catalyst activity decreases significantly on each recycling step. This can be attributed, inter alia, to the homogeneous catalyst not remaining fully immobilized. The preparation of the economically attractive formamide is not described in this study.

The use of heterogeneous hydrogenation catalysts can make simple isolation and reuse of the catalyst possible. U.S. Pat. No. 4,269,998 describes the use of copper chromite catalysts in combination with group VIII compounds for the preparation of dialkylformamides. A disadvantage is that only dialkylformamides can be obtained by this process. The preparation of formamide or formic esters is not described. In addition, the group VIII compounds are sensitive to carbon monoxide. However, carbon monoxide is frequently present as impurity in the hydrogen or carbon dioxide used. Thus, high-purity hydrogen and high-purity carbon dioxide have to be used in this process.

J. Liu, G. Guo, Z. Zhang, T. Jiang, H. Liu, J. Song, H. Fan, B. Han, Chem. Commun. 2010, 46, 5770-5772, describe copper/zinc oxide catalysts without a group VIII compound for preparing dimethylformamide. A disadvantage of this process is likewise that only dimethylformamide can be obtained. The preparation of formamide or formic esters is not described.

DETAILED DESCRIPTION OF THE INVENTION

Figure 1:
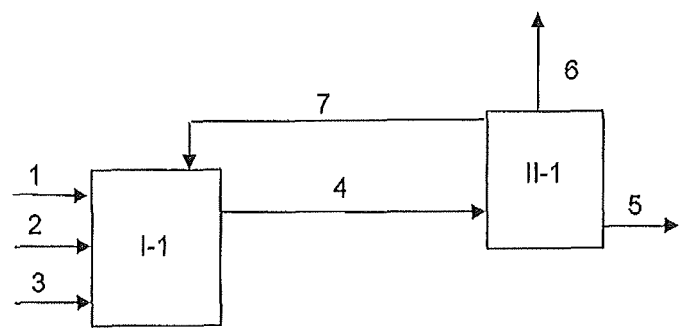
FIG. 1 shows a block diagram of a plant for a preferred embodiment of the process of the invention for preparing formamide compounds (Ia2) from carbon dioxide, hydrogen and an amine (Ic).

It is an object of the present invention to provide a process for preparing carboxylic acid derivatives, in particular formamide and N-substituted formamide derivatives and formic esters on the basis of the starting materials carbon dioxide, hydrogen and an amine or an alcohol. The process should preferably be able to be operated continuously. The preparation of the carboxylic acid derivatives, in particular formamide and N-substituted formamide derivatives and formic esters, should preferably occur in one reaction step (integrated process). The target products, i.e. formamide, the N-substituted formamide derivatives and the formic esters, should be able to be obtained in high yields and selectivities. The work-up of the reaction output from the hydrogenation reactor and the removal of the catalyst should be technically simple, require little energy and preferably be carried out using exclusively materials which are in any case present in the process, without additional auxiliaries.

This object is achieved by a process for preparing carboxylic acid derivatives of the general formula (Ia)

$$H-(C=O)-R \qquad (Ia),$$

where
R is selected from the group consisting of $OR^1$ and $NR^2R^3$,
where
$R^1$ is unsubstituted or at least monosubstituted $C_1$-$C_{15}$-alkyl, $C_5$-$C_{10}$-cycloalkyl, $C_5$-$C_{10}$-heterocyclyl, $C_5$-$C_{10}$-aryl or $C_5$-$C_{10}$-heteroaryl, where the substituents are selected from the group consisting of $C_1$-$C_{15}$-alkyl, $C_1$-$C_6$-alkoxy, $C_5$-$C_{10}$-cycloalkyl and $C_5$-$C_{10}$-aryl;

$R^2$ and $R^3$ are each, independently of one another, hydrogen, unsubstituted or at least monosubstituted $C_1$-$C_{15}$-alkyl, $C_5$-$C_{10}$-cycloalkyl, $C_5$-$C_{10}$-heterocyclyl, $C_5$-$C_{10}$-aryl or $C_5$-$C_{10}$-heteroaryl, where the substituents are selected from the group consisting of $C_1$-$C_{15}$-alkyl, $C_5$-$C_{10}$-cycloalkyl and $C_5$-$C_{10}$-aryl or $R^2$ and $R^3$ together with the nitrogen atom form a five- or six-membered ring which optionally additionally comprises one or more heteroatoms selected from among O, S and N and bearing the substituent $R^4$, where $R^4$ is hydrogen or $C_1$-$C_6$-alkyl;

by reaction of a reaction mixture (Rm) comprising carbon dioxide, hydrogen and an alcohol of the general formula (Ib)

$$R^1\text{—OH} \quad (Ib)$$

where $R^1$ has the above meanings, or an amine of the general formula (Ic)

$$NHR^2R^3 \quad (Ic)$$

where $R^2$ and $R^3$ each independently have the above meanings, in the presence of a catalyst comprising gold at a pressure in the range from 0.2 to 30 MPa and a temperature in the range from 20 to 200° C. in a hydrogenation reactor.

The process of the invention makes it possible to use the inexpensive carbon dioxide instead of the comparatively costly carbon monoxide as $C_1$ building block. In addition, the process of the invention allows simple removal of the catalyst, good product yields and simple work-up of the product mixture.

In the process of the invention, a reaction mixture (Rm) comprising carbon dioxide, hydrogen, an alcohol (Ib) or an amine (Ic) is reacted. When a reaction mixture (Rm) comprising an alcohol (Ia) is used, a formic ester (Ia1) is formed as carboxylic acid derivative (Ia) according to the general reaction equation (II), where the abovementioned definitions of $R^1$ apply analogously to the formic ester (Ia1). That is to say, one mole of formic ester (Ia1) and one mole of water of reaction are formed from one mole of carbon dioxide, one mole of hydrogen and one mole of alcohol (Ib).

When a reaction mixture (Rm) comprising an amine (Ia) is used, a formamide compound (Ia2) is formed as carboxylic acid derivative (Ia) according to the general reaction equation (III), where the abovementioned definitions of $R^2$ and $R^3$ apply analogously to the formamide compound (Ia2). That is to say, one mole of formamide compound (Ia2) and one mole of water of reaction are formed from one mole of carbon dioxide, one mole of hydrogen and one mole of amine (Ic).

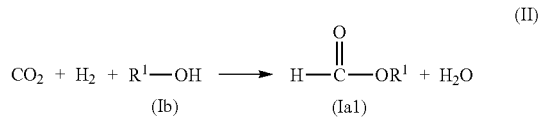

(II)

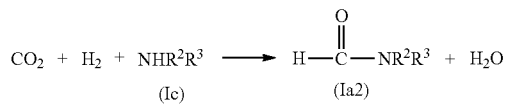

(III)

In a preferred embodiment, alcohols $R_1$—OH (Ib) in which $R^1$ is unsubstituted or at least monosubstituted $C_1$-$C_8$-alkyl, where the substituents are selected from the group consisting of $C_1$-$C_6$-alkyl and $C_1$-$C_6$-alkoxy.

are used for the preparation of formic esters (Ia1).

Here, the corresponding formic esters of the general formula (Ia1)

$$H(C{=}O)\text{—}OR^1 \quad (Ia1)$$

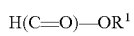

in which $R^1$ is unsubstituted or at least monosubstituted $C_1$-$C_8$-alkyl
where the substituents are selected from the group consisting of $C_1$-$C_6$-alkyl and $C_1$-$C_6$-alkoxy, are obtained.

For the purposes of the present invention, the term $C_1$-$C_{15}$-alkyl refers to branched, unbranched, saturated and unsaturated groups. Preference is given to saturated alkyl groups having from 1 to 6 carbon atoms ($C_1$-$C_6$-alkyl). Greater preference is given to saturated alkyl groups having from 1 to 4 carbon atoms ($C_1$-$C_4$-alkyl).

Examples of saturated alkyl groups are methyl, ethyl, n-propyl, isopropyl, n-butyl, isobutyl, sec-butyl, tert-butyl, amyl and hexyl.

Examples of unsaturated alkyl groups (alkenyl, alkynyl) are vinyl, allyl, butenyl, ethynyl and propynyl.

The $C_1$-$C_{15}$-alkyl group can be unsubstituted or substituted by one or more substituents selected from the group consisting of $C_1$-$C_{15}$-alkyl, $C_1$-$C_6$-alkoxy, $C_5$-$C_{10}$-cycloalkyl, $C_5$-$C_{10}$-aryl.

For the present purposes, the term $C_5$-$C_{10}$-cycloalkyl refers to saturated, unsaturated monocyclic and polycyclic groups. Examples of $C_5$-$C_{10}$-cycloalkyl are cyclopentyl, cyclohexyl and cycloheptyl. The cycloalkyl groups can be unsubstituted or substituted by one or more substituents as defined above for the $C_1$-$C_{15}$-alkyl group.

For the purposes of the present invention, $C_5$-$C_{10}$-aryl is an aromatic ring system having from 5 to 10 carbon atoms. The aromatic ring system can be monocyclic or bicyclic. Examples of aryl groups are phenyl, naphthyl such as 1-naphthyl and 2-naphthyl. The aryl group can be unsubstituted or substituted by one or more substituents as defined above for $C_1$-$C_{15}$-alkyl.

For the purposes of the present invention, $C_5$-$C_{10}$-heteroaryl is a heteroaromatic system comprising at least one heteroatom selected from the group consisting of N, O and S. The heteroaryl groups can be monocyclic or bicyclic. When nitrogen is a ring atom, the present invention also comprises N-oxides of the nitrogen-comprising heteroaryls. Examples of heteroaryls are thienyl, benzothienyl, 1-naphthothienyl, thianthrenyl, furyl, benzofuryl, pyrrolyl, imidazolyl, pyrazolyl, pyridyl, pyrazinyl, pyrimidinyl, pyridazinyl, indolyl, isoindolyl, indazolyl, purinyl, isoquinolinyl, quinolinyl, acridinyl, naphthyridinyl, quinoxalinyl, quinazolinyl, cinnolinyl, piperidinyl, carbolinyl, thiazolyl, oxazolyl, isothiazolyl, isoxazolyl. The heteroaryl groups can be unsubstituted or substituted by one or more substituents as defined above for $C_1$-$C_{15}$-alkyl.

For the purposes of the present invention, the term $C_5$-$C_{10}$-heterocyclyl refers to five- to ten-membered ring systems comprising at least one heteroatom from the group consisting of N, O and S. The ring systems can be monocyclic or bicyclic. Examples of suitable heterocyclic ring systems are piperidinyl, pyrrolidinyl, pyrrolinyl, pyrazolinyl, pyrazolidinyl, morpholinyl, thiomorpholinyl, pyranyl, thiopyranyl, piperazinyl, indolinyl, dihydrofuranyl, tetrahydrofuranyl, dihydrothiophenyl, tetrahydrothiophenyl, dihydropyranyl and tetrahydropyranyl.

for the purposes of the present invention, the term $C_1$-$C_6$-alkoxy refers to $C_1$-$C_6$-alkyl-O-radicals. As examples of alkyl part of the alkoxy group, mention may be made of methyl, ethyl, n-propyl, isopropyl, n-butyl, isobutyl, sec-butyl, tert-butyl, amyl and hexyl.

Particular preference is given to using an alcohol selected from the group consisting of methanol, ethanol, 2-methoxyethanol, 1-propanol, 2-propanol, 1-butanol, 2-butanol, 2-methyl-1-propanol, 1-pentanol, 1-hexanol, 1-heptanol and 1-octanol as alcohol (Ib). In this way, the corresponding formic esters (Ia1) selected from the group consisting of methyl formate, ethyl formate, 2-methoxyethyl formate, 1-propyl formate, 2-propyl formate, 1-butyl formate, 2-butyl formate, 2-methyl-1-propyl formate, 1-pentyl formate, 1-hexyl formate, 1-heptyl formate, 1-octyl formate can be obtained.

In a further preferred embodiment, methanol is used as alcohol (Ib) and methyl formate is obtained as formic ester (Ia1).

For the purposes of the present invention, the term "formamide compound (Ia2)" encompasses both formamide (H—(C=O)—$NH_2$) itself and N-substituted formamide derivatives. In a preferred embodiment, an amine selected from the group consisting of ammonia, methylamine, dimethylamine, ethylamine, diethylamine, n-propylamine, di-n-propylamine, isopropylamine, diisopropylamine, n-butylamine, di-n-butylamine, isobutylamine, diisobutylamine, morpholine, piperidine and piperazine is used as amine (Ic) for the preparation of formamide compounds (Ia2). In this way, the corresponding formamide compounds (Ia2) selected from the group consisting of formamide, methylformamide, dimethylformamide, ethylformamide, diethylformamide, n-proypylformamide, di-n-propylformamide, isopropylformamide, diisopropylformamide, n-butylformamide, di-n-butylformamide, isobutylformamide, diisobutylformamide, N-formylmorpholine, N-formylpiperidine and N-formylpiperazine can be obtained.

In a further preferred embodiment, an amine selected from the group consisting of ammonia, methylamine and dimethylamine is used as amine (Ic). In this way, the corresponding formamide compounds (Ia2) selected from the group consisting of formamide, methylformamide, dimethylformamide can be obtained.

In a particularly preferred embodiment, ammonia is used as amine (Ic) and formamide is obtained as formamide compound (Ia2).

In a further particularly preferred embodiment, morpholine is used as amine (Ic) and formylmorpholine is obtained as formamide compound (Ia2).

As hydrogenation reactors, it is in principle possible to use all reactors which are basically suitable for heterogeneously catalyzed gas/liquid reactions at the given temperature and the given pressure. Suitable standard reactors for gas-liquid reaction systems are described, for example, in K. D. Henkel, "Reactor Types and Their Industrial Applications" and in Ullmann's Encyclopedia of Industrial Chemistry, 2005, Wiley-VCH Verlag GmbH & Co. KGaA, DOI: 10.1002/14356007.b04_087. Examples which may be mentioned are stirred tank reactors, tube reactors, shell-and-tube reactors and fixed-bed reactors.

The amines (Ic) or alcohols (Ib) used in the process of the invention are fed in liquid or gaseous form into the hydrogenation reactor. The molar ratio of the alcohol (Ib) or amine (Ic) used in the process of the invention to the carbon dioxide used is generally from 0.01 to 30 and preferably from 0.2 to 5.

The carbon dioxide used in the reaction of carbon dioxide with hydrogen in the hydrogenation reactor can be used in solid, liquid or gaseous form. It is also possible to use industrially available gas mixtures comprising carbon dioxide. The hydrogen and the carbon dioxide can also comprise other inert gases such as nitrogen or noble gases. It has surprisingly been found that the gold catalysts used in the process of the invention are tolerant to carbon monoxide which often leads to poisoning of hydrogenation catalysts. The hydrogen used in the reaction in the hydrogenation reactor and the carbon dioxide can therefore also comprise carbon monoxide as impurity. The carbon monoxide content in the gas streams fed to the hydrogenation reactor is advantageously below 20 mol % based on the total amount of carbon dioxide and hydrogen in the hydrogenation reactor. Although larger amounts are optionally likewise still tolerable, they generally require the use of a higher pressure in the reactor, which makes further compression energy necessary.

The hydrogenation of carbon dioxide occurs in the liquid phase preferably at a temperature of from 20 to 200° C. and a total pressure of from 0.2 to 30 MPa abs, with the total pressure preferably being at least 1 MPa abs. and particularly preferably at least 5 MPa abs and also preferably not more than 15 MPa abs. The temperature is preferably at least 30° C. and particularly preferably at least 100° C. and also preferably not more than 180° C., particularly preferably not more than 170° C. and very particularly preferably not more than 160° C.

The partial pressure of carbon dioxide is generally at least 0.5 MPa and preferably at least 2 MPa and also generally not more than 8 MPa. The partial pressure of hydrogen is generally at least 0.5 MPa and preferably at least 1 MPa and also generally not more than 25 MPa and preferably not more than 15 MPa.

The molar ratio of hydrogen to carbon dioxide in the feed to the hydrogenation reactor is preferably from 0.1 to 10 and particularly preferably from 1 to 3.

The molar ratio of carbon dioxide to amine (Ic) or alcohol (Ib) in the feed to the hydrogenation reactor is generally from 0.01 to 30 and preferably from 0.2 to 5.

The catalyst used in the process of the invention comprises a catalytically active metal component comprising gold. Preference is given to using a heterogeneous catalyst. Gold is preferably present in metallic form, i.e. oxidation state (0). The metal component of the catalyst can comprise not only gold but also one or more further metals, for example noble metals selected from the group consisting of Pd, Pt, Ag and Cu, in the form of alloys. The metal component can further comprise metal promoters. Preference is given to using gold in pure form as metal component, i.e. a metal component comprising at least 50% by weight, preferably at least 70% by weight and in particular 90% by weight, of gold, in each case based on the total weight of the metal component.

The metal component of the catalyst is preferably used in the form of nanoparticles. The average particle diameter ($D^{50}$) is usually in the range from 0.1 to 50 nm.

The metal component of the catalyst can be used as such. In this case, the metal component itself forms the actual catalyst, i.e. the metal component of the catalyst is used in unsupported form.

A suitable heterogeneous catalyst is, for example, gold itself, i.e. in pure form, or gold on a support material (supported gold). In the case of gold itself, preference is given to using "Gold Black", i.e. colloidally precipitated elemental gold.

It is also possible to use a catalyst comprising the metal component and a support material (supported catalyst). The metal component is then immobilized on the surface of the support material. Supported gold nanoparticles can likewise be used.

It is also possible to use gold alloys such as Au-M on supports, where M is a noble metal such as Pd or Pt or else another metal such as Ag or Cu, as catalysts. Different metal promoters can also be present in one and the same catalyst.

Preference is given to using supported gold catalysts in the process of the invention. As supports, it is possible to use a wide variety of materials such as inorganic oxides, graphite, polymers or metal. In the case of inorganic oxides, preference is given to silicon dioxide, magnesium oxide, zirconium oxide and/or titanium oxide. Magnesium oxide, aluminum oxide, silicon oxide, gallium oxide, zirconium oxide, cerium oxide and/or titanium oxide are particularly preferred as support materials. It is also possible to use mixtures of various inorganic oxides. The heterogeneous catalyst can be used in a variety of geometric shapes and sizes, for example pellets, cylinders, hollow cylinders, spheres, rods or extrudates. The average particle diameter is usually in the range from 1 to 10 mm. In the case of metals or polymers as supports, meshes, woven mesh wires or knitteds can also be employed.

In the case of a supported catalyst, the heterogeneous catalyst generally comprises from 0.01 to 50% by weight, preferably from 0.1 to 20% by weight and particularly preferably from 0.1 to 5% by weight, of gold based on the total mass of the supported catalyst used. In the case of an unsupported catalyst, the gold content is generally in the range from 0.01 to 100% by weight based on the total amount of catalyst used.

Suitable gold catalysts are commercially available or can be obtained by known methods by treatment of a support material with the solution of a gold compound or by coprecipitation with subsequent drying, heat treatment and/or calcination.

Regardless of whether the gold-comprising catalyst is supported or not and regardless of whether further metals are comprised (e.g. in the form of gold alloys), the gold catalyst generally comprises gold particles having a diameter of from 0.1 to 50 nm, measured by X-ray diffraction. In addition, particles having a diameter of less than 0.1 nm or else particles larger than 50 nm can also be present.

Furthermore, regardless of whether the gold-comprising catalyst is supported or not and regardless of whether further metals are comprised (e.g. in the form of gold alloys), the heterogeneous catalyst has a BET surface area in the range from 1 $m^2/g$ to 1000 $m^2/g$ (determination of the BET surface area in accordance with DIN ISO 9277). The BET surface area of the heterogeneous catalyst is preferably in the range from 10 $m^2/g$ to 500 $m^2/g$.

The volume of the heterogeneous catalyst in the hydrogenation reactor is generally in the range from 0.1 to 95% of the reaction volume of the hydrogenation reactor, where the catalyst volume is given by the catalyst mass divided by the bulk density of the catalyst.

In the process of the invention, the reaction mixture (Rm) can additionally comprise a polar solvent. This is advantageous particularly when an amine (Ic) is reacted with carbon dioxide and hydrogen to form a formamide compound (Ia2) according to the general reaction equation (III). Amines (Ic), for example ammonia, can form salts with carbon dioxide. The use of a polar solvent enables the solubility of these salts in the reaction mixture (Rm) to be improved.

In the process of the invention, the reaction mixture (Rm) can comprise a polar solvent or mixtures of two or more polar solvents. As classes of substances which are suitable as polar solvents, preference is given to alcohols and diols and formic esters thereof, formamides such as formamide, methylformamide or dimethylformamide or water.

Suitable alcohols are, for example, methanol, ethanol, 2-methoxyethanol, 1-propanol, 2-propanol, 1-butanol, 2-butanol and 2-methyl-1-propanol.

As classes of substances which are suitable as polar solvents, preference is given to diols and formic esters thereof, polyols and formic esters thereof, sulfones, sulfoxides, open-chain or cyclic amides and mixtures of the classes of substances mentioned.

Suitable diols and polyols are, for example, ethylene glycol, diethylene glycol, triethylene glycol, polyethylene glycol, 1,3-propanediol, 2-methyl-1,3-propanediol, 1,4-butanediol, dipropylene glycol, 1,5-pentanediol, 1,6-hexanediol and glycerol.

A suitable sulfone is tetramethylene sulfone (sulfolane).

Suitable sulfoxides are, for example, dialkyl sulfoxides, preferably $C_1$-$C_6$-dialkyl sulfoxides, in particular dimethyl sulfoxide.

Suitable open-chain or cyclic amides are, for example, formamide, methylformamide, dimethylformamide, N-methylpyrrolidone, acetamide and N-methylcaprolactam.

The molar ratio of the polar solvent or solvent mixture to be used in the process of the invention to the amine (Ic) used is generally from 0.5 to 30 and preferably from 1 to 20. The hydrogenation of carbon dioxide in the process of the invention can be carried out batchwise or continuously. In a batch process, the reactor is charged with the desired liquid and optionally solid starting materials and auxiliaries and subsequently pressurized with carbon dioxide and hydrogen to the desired pressure and the desired temperature. After conclusion of the reaction, the reactor is generally depressurized and the liquid reaction mixture is separated off from the heterogeneous catalyst.

In a continuous process, the starting materials and auxiliaries, including carbon dioxide and hydrogen, are fed continuously to the hydrogenation reactor. The catalyst can be used as a fixed bed (fixed-bed reactor). In the case of a fixed-bed reactor, the heterogeneous catalyst is fixed in position in the hydrogenation reactor.

It is also possible to suspend the catalyst in the reaction mixture (Rm). In the case of a suspended heterogeneous catalyst, this can be present in the hydrogenation reactor before commencement of the reaction. However, in a continuous process, the heterogeneous catalyst is preferably fed into the hydrogenation reactor at the same rate as it is taken continuously from the reactor.

In a continuous process, a liquid phase is discharged continuously from the hydrogenation reactor so that the liquid level in the reactor remains the same on average. Preference is given to the continuous hydrogenation of carbon dioxide.

The average residence time of the reaction mixture (Rm) in the hydrogenation reactor is generally from 10 minutes to 5 hours.

Regardless of the type of heterogeneous catalyst and regardless of whether the hydrogenation is carried out continuously or batchwise, a hydrogenation mixture (H) comprising the carboxylic acid derivative (Ia), water of reaction and possibly unreacted alcohol (Ib) or unreacted amine (Ic) is obtained in the reaction of the reaction mixture (Rm) in the hydrogenation reactor. The hydrogenation mixture (H) can additionally comprise the polar solvent or polar solvent mixture. If a suspended heterogeneous catalyst is used, this is likewise comprised in the hydrogenation mixture (H).

In the case of a fixed-bed catalyst, the catalyst usually remains in the hydrogenation reactor due to it being fixed in position and the hydrogenation mixture does not comprise any catalyst, i.e. less than 5 ppm of gold catalyst based on the total weight of the reaction mixture (Rm). In the case of suspended heterogeneous catalysts which are not fixed in position, these are usually held back in the hydrogenation reactor by means of known measures, e.g. meshes or filters, at the reactor outlet. However, the catalyst can also be separated off from the hydrogenation mixture (H) after the reaction by means of simple meshes such as filtration, decantation or centrifugation in a downstream step and recirculated to the hydrogenation reactor. After the catalyst has been separated off, the hydrogenation mixture (H) is virtually free of gold (worked up hydrogenation mixture (Hw)), i.e. the gold content of the worked up hydrogenation mixture (Hw) is less than 5 ppm by weight based on the worked up hydrogenation mixture (Hw).

After the catalyst has been separated off, the worked up hydrogenation mixture (Hw) is worked up by distillation to give a first stream comprising the carboxylic acid derivative (Ia), a second stream comprising unreacted alcohol (Ib) or unreacted amine (Ic) and a third stream comprising the water of reaction.

If the reaction is carried out in the presence of a polar solvent, the latter can be separated off via a fourth stream. However, it is also possible for the polar solvent to be separated off together with the unreacted alcohol (Ib) or unreacted amine (Ic) (second stream). In addition, it is possible for the polar solvent to be separated off together with the water of reaction (third stream).

The work-up by distillation can, depending on the separation problem, be carried out in one, two or more stages.

In the preparation of formamide compounds (Ia2) in the presence of a polar solvent, the distillation to separate off low-boiling polar solvents such as the monohydric alcohols methanol, ethanol, propanols and butanols can be carried out at atmospheric pressure or under reduced pressure. In a preferred embodiment, the polar solvents are recirculated to the hydrogenation reactor.

Even when low-boiling carboxylic acid derivatives (Ia) such as methyl formate, ethyl formate or propyl formate are prepared, these are preferably separated off from the water of reaction and unreacted alcohol (Ib) at atmospheric pressure or slightly superatmospheric pressure (up to a gauge pressure of 0.2 MPa). Unreacted alcohol $R^1$—OH is, in a preferred embodiment, recirculated to the hydrogenation reactor and the water of reaction is discarded.

On the other hand, when diols are used as polar solvents and relatively high-boiling carboxylic acid derivatives (Ia) such as formamides are obtained, the work-up by distillation is preferably carried out under reduced pressure, more preferably in the range from 0.1 to 500 mbar abs. Unreacted amine (Ic) is, in a preferred embodiment, separated off in the distillation and recirculated to the hydrogenation reactor. Likewise, any polar solvent used is, in a preferred embodiment, recirculated to the hydrogenation reactor after the distillation. The water of reaction which is separated off is discarded. Various apparatuses are possible, depending on the separation problem, as distillation units for the work-up by distillation of the worked up hydrogenation mixture (Hw). If the boiling points of the participating materials, viz. carboxylic acid derivative (Ia), unreacted alcohol (Ib) or unreacted amine (Ic) and any polar solvent, are wide apart, it is possible to use, for example, evaporators such as falling film evaporators. However, the distillation unit to be used generally comprises a distillation column comprising random packing elements, ordered packing and/or trays.

When an additional polar solvent is used, the distillation unit comprises at least one distillation column, preferably two or three distillation columns. These columns comprise, depending on the separation problem, for example random packing elements, ordered packing and/or trays.

The carboxylic acid derivatives (Ia) (target products) are discharged from the process and, if necessary, passed to a fine purification, preferably by distillation The invention is illustrated with the aid of the following figures, without being restricted thereto.

The figures show in detail:

FIG. 1 a block diagram of a plant for a preferred embodiment of the process of the invention for preparing formamide compounds (Ia2) from carbon dioxide, hydrogen and an amine (Ic)

Figure 2:
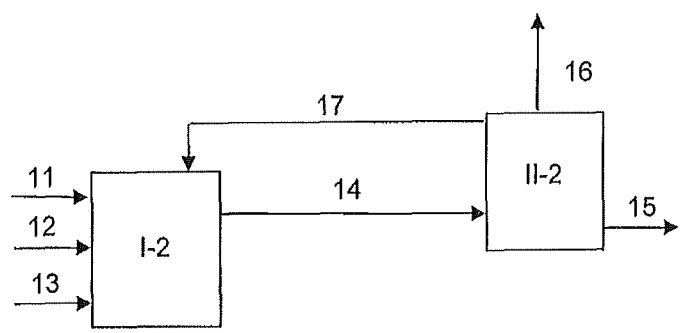
FIG. 2 shows a block diagram of a plant for a preferred embodiment of the process of the invention for preparing formic esters (Ia1) from carbon dioxide, hydrogen and an alcohol (Ib).

FIG. 2 shows a block diagram of a plant for a preferred embodiment of the process of the invention for preparing formic esters (Ia1) from carbon dioxide, hydrogen and an alcohol (Ib)

Figure 3:
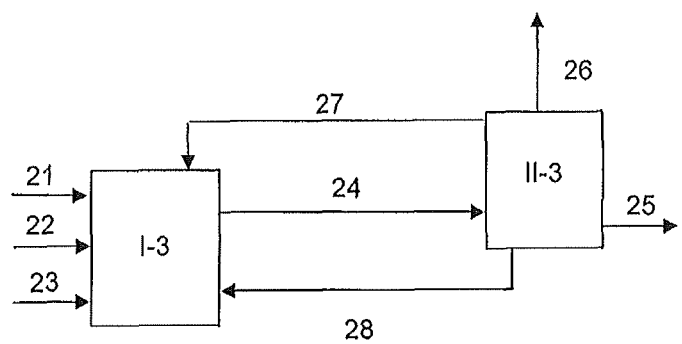
FIG. 3 shows a block diagram of a plant for a preferred embodiment of the process of the invention for preparing formamide compounds (Ia2) from carbon dioxide, hydrogen and an amine (Ic) with addition of a polar solvent.

FIG. 3 shows a block diagram of a plant for a preferred embodiment of the process of the invention for preparing formamide compounds (Ia2) from carbon dioxide, hydrogen and an amine (Ic) with addition of a polar solvent.

In FIGS. 1, 2 and 3, the reference numerals have the following meanings:

FIG. 1
I-1 hydrogenation reactor
II-1 distillation unit
1 stream comprising carbon dioxide
2 stream comprising hydrogen
3 stream comprising amine (Ic)
4 stream comprising formamide compound (Ia2), water of reaction, unreacted amine (Ic); worked up hydrogenation mixture (Hw)
5 stream comprising formamide compound (Ia2); target product; first stream
6 stream comprising water of reaction; third stream
7 stream comprising unreacted amine (Ic), second stream
FIG. 2
I-2 hydrogenation reactor
II-2 distillation unit
11 stream comprising carbon dioxide
12 stream comprising hydrogen
13 stream comprising alcohol (Ib)
14 stream comprising formic ester (Ia1), water of reaction, unreacted alcohol (Ib); worked up hydrogenation mixture (Hw)
15 stream comprising formic ester (Ia2); target product; first stream
16 stream comprising water of reaction; third stream
17 stream comprising unreacted amine (Ic), second stream
FIG. 3
I-3 hydrogenation reactor
II-3 distillation unit
21 stream comprising carbon dioxide
22 stream comprising hydrogen
23 stream comprising amine (Ic)

24 stream comprising formamide compound (Ia2), water of reaction, polar solvent, unreacted amine (Ic); worked up hydrogenation mixture (Hw)

25 stream comprising formamide compound (Ia2); target product; first stream 26 stream comprising water of reaction; third stream 27 stream comprising unreacted amine (Ic), second stream 28 stream comprising polar solvent In the embodiment shown in FIG. 1, carbon dioxide, stream 1, hydrogen, stream 2, and the amine (Ic), stream 3, are fed into the hydrogenation reactor I-1. In this, the streams are reacted in the presence of the heterogeneous gold catalyst to give the formamide compound (Ia2) and water of reaction. The heterogeneous catalyst is separated off from the liquid hydrogenation mixture (H) comprising the formamide compound (Ia2), water of reaction, the heterogeneous catalyst and unreacted amine (Ic). The worked up hydrogenation mixture (Hw) obtained in this way is fed as stream 4 to the distillation unit II-1. In this, the worked up hydrogenation mixture (Hw) is fractionally distilled to give the formamide compound (Ia2), stream 5, discharge of water of reaction, stream 6, and unreacted amine (Ic), stream 7, which is recirculated to the hydrogenation reactor II-1.

In the embodiment shown in FIG. 2, carbon dioxide, stream 11, hydrogen, stream 12, and the alcohol (Ib), stream 13, are fed into the hydrogenation reactor I-2. In this, the streams are reacted in the presence of the heterogeneous gold catalyst to give the formic ester (Ia1) and water of reaction. The heterogeneous catalyst is separated off from the liquid hydrogenation mixture (H) comprising the formic ester (Ia1), water of reaction, the heterogeneous catalyst and unreacted alcohol (Ib). The worked up hydrogenation mixture (Hw) obtained in this way is fed as stream 14 to the distillation unit II-2. In this, the worked up hydrogenation mixture (Hw) is fractionally distilled to give the formic ester (Ia1), stream 15, discharge of water of reaction, stream 6, and unreacted alcohol (Ib), stream 17, which is recirculated to the hydrogenation reactor II-2.

In the embodiment shown in FIG. 3, carbon dioxide, stream 21, hydrogen, stream 22, and the amine (Ic), stream 23, are fed into the hydrogenation reactor I-3 which also comprises a polar solvent. In the reactor, the streams are reacted in the presence of the heterogeneous gold catalyst to give a formamide compound (Ia2) and water of reaction. The heterogeneous catalyst is separated off from the liquid hydrogenation mixture (H) comprising the formamide compound (Ia2), water of reaction, polar solvent, the heterogeneous catalyst and unreacted amine (Ic). The worked up hydrogenation mixture (Hw) obtained in this way is fed as stream 44 to the distillation unit II-3. In this, the worked up hydrogenation mixture (Hw) is fractionally distilled to give the formamide compound (Ia2), stream 25, discharge of water of reaction, stream 26, and unreacted amine (Ic), stream 27, which is recirculated to the hydrogenation reactor II-3 and also the polar solvent which is likewise recirculated as stream 28 to the hydrogenation reactor II-3.

The invention is illustrated below with the aid of examples, without being restricted thereto.

EXAMPLES

A 250 ml autoclave made of Hastelloy C and equipped with a magnetic stirrer bar was charged under inert conditions with the starting materials indicated in each case in Table 1 below (alcohol (Ib) or amine (Ic)) and the heterogeneous gold catalyst which was located in a catalyst basket. In the synthesis of formic esters, the corresponding alcohol or when using liquid amines, the latter, was introduced. The autoclave was subsequently closed and pressurized at room temperature with carbon dioxide ($CO_2$), hydrogen ($H_2$) and optionally ammonia or dimethylamine and the reactor was heated while stirring (700 rpm). After the appropriate reaction time, the reactor was cooled and the reaction mixture was depressurized. The catalyst remained in the catalyst basket. The composition of the reaction solution (worked up hydrogenation mixture (Hw)) was determined by gas chromatography, and gold content was determined by atomic absorption spectroscopy (AAS). The parameters and results of the individual experiments are shown in Table 1.

Examples A-1 to A-11 show that formamides and formic esters can be obtained easily by hydrogenation of $CO_2$ using the gold catalysts. No gold, within the detection limit, can be found in the reaction solution (worked up hydrogenation mixture (Hw)), which makes it possible for the catalyst to be separated off and recirculated very simply.

| | Example A1 | Example A2 | Example A3 | Example A4 |
|---|---|---|---|---|
| Autoclave | 250 ml | 250 ml | 250 ml | 250 ml |
| Polar solvent | 70 g of methanol | — | — | — |
| Starting material (amine (Ic) or alcohol (Ib)) | 9.5 g of ammonia | 70 g of methanol | 70 g of methanol | 80 g of dimethylamine |
| Catalyst | 5 g of Aurolite 1% Au on $TiO_2$ | 5 g of Aurolite 1% Au on $TiO_2$ | 5 g of Aurolite 1% Au on $Al_2O_3$ | 5 g of Aurolite 1% Au on $TiO_2$ |
| Injection of $CO_2$ | 20.1 g | 20.0 g | 20.0 g | 29.9 g |
| Injection of $H_2$ | to 140 bar | to 200 bar | to 200 bar | to 140 bar |
| Heating | 125° C. | 125° C. | 140° C. | 125° C. |
| Reaction time | 10 h | 10 h | 10 h | 10 h |
| Yield of reaction output (worked up hydrogenation mixture (Hw)) | 92.3 g | 69.9 g | 67.1 g | 97.8 g |
| Product content (content of carboxylic acid derivative (Ia)) | 10.3% of formamide | 5.2% of methyl formate | 4.4% of methyl formate | 56.0% of dimethylformamide |
| Gold content of the reaction solution (worked up | <1 ppm | not determined | not determined | <1 ppm |

-continued

| | Example A5 | Example A6 | Example A7 |
|---|---|---|---|
| Autoclave | 250 ml | 250 ml | 250 ml |
| Polar solvent | — | 70 g of methanol | — |
| Starting material (amine (Ic) or alcohol (Ib)) | 80 g of dimethylamine | 9.3 g of ammonia | 70 g of methanol |
| Catalyst | 5 g of Aurolite 1% Au on $TiO_2$ | 5 g of Aurolite 1% Au on $TiO_2$ | 5 g of Aurolite 1% Au on $Al_2O_3$ |
| Injection of $CO_2$ | 30.3 g | 20.2 g | 25.1 g |
| Injection of $H_2$ | to 200 bar | to 200 bar | to 200 bar |
| Heating | 140° C. | 140° C. | 150° C. |
| Reaction time | 10 h | 10 h | 10 h |
| Yield of reaction output (worked up hydrogenation mixture (Hw)) | 92.2 g | 96.3 g | 69.1 g |
| Product content (content of carboxylic acid derivative (Ia)) | 28.8% of dimethylformamide | 10.7% of formamide | 4.1% of methyl formate |
| Gold content of the reaction solution (worked up hydrogenation mixture (Hw)) | not determined | not determined | <1 ppm |

| | Example A8 | Example A9 | Example A10 | Example A11 |
|---|---|---|---|---|
| Autoclave | 250 ml | 250 ml | 250 ml | 250 ml |
| Polar solvent | — | — | — | 70 g of methanol |
| Starting material (amine (Ic) or alcohol (Ib)) | 80 g of ethanol | 80 g of dibutylamine | 80 g of dimethylamine | 9.8 g of ammonia |
| Catalyst | 5 g of Aurolite 1% Au on $TiO_2$ | 5 g of Aurolite 1% Au on $TiO_2$ | 5 g of Aurolite 1% Au on $Al_2O_3$ | 5 g of Aurolite 1% Au on $Al_2O_3$ |
| Injection of $CO_2$ | 20.1 g | 20.0 g | 30.3 g | 20.0 g |
| Injection of $H_2$ | to 200 bar | to 200 bar | to 200 bar | to 200 bar |
| Heating | 125° C. | 125° C. | 140° C. | 140° C. |
| Reaction time | 10 h | 10 h | 10 h | 10 h |
| Yield of reaction output (worked up hydrogenation mixture (Hw)) | 79.5 g | 85.7 g | 67.1 g | 90.6 g |
| Product content (content of carboxylic acid derivative (Ia)) | 2.5% ethylformiate | 15.3% dibutylformamide | 5.2% dimethylformamide | 3.3% formamide |
| Gold content of the reaction solution (worked up hydrogenation mixture (Hw)) | not determined | not determined | not determined | not determined |

Comparative Experiments:

| | Example A12 | Example A13 |
|---|---|---|
| Autoclave | 250 ml | 250 ml |
| Polar solvent | 70.0 g of methanol | 70.0 g of methanol |
| Starting material (amine (Ic) or alcohol (Ib)) | 9.8 g of ammonia | 9.1 g of ammonia |
| Catalyst | 0.5 g of Raney nickel | 5 g of palladium on carbon (1% Pd) |
| Injection of $CO_2$ | 21.2 g | 19.3 g |
| Injection of $H_2$ | to 140 bar | to 140 bar |
| Heating | 125° C. | 125° C. |
| Reaction time | 10 h | 10 h |
| Yield of reaction output (worked up hydrogenation mixture (Hw)) | 88.3 g | 96.1 g |
| Product content (content of carboxylic acid derivative (Ia)) | 0% of formamide | 0.8% of formamide |
| Metal content of the reaction solution (worked up hydrogenation mixture (Hw)) | 790 ppm of nickel | 1 ppm of palladium |

Comparative examples A12 and A13 show that when standard hydrogenation catalysts such as Raney nickel or palladium on carbon are used under conditions otherwise identical to those in the case of the gold catalysts, no formamide (in the case of Raney nickel) or only significantly poorer yields (factor of 15 in the case of Pd) can be achieved. This shows the advantage of the use of the catalysts according to the invention for this reaction.

The invention claimed is:

1. A process for preparing carboxylic acid derivatives of the general formula (Ia)

$$H-(C=O)-R \quad (Ia),$$

where
R is selected from the group consisting of $OR^1$ and $NR^2R^3$,
where
$R^1$ is unsubstituted or at least monosubstituted $C_1$-$C_{15}$-alkyl, $C_5$-$C_{10}$-cycloalkyl, $C_5$-$C_{10}$-heterocyclyl, $C_5$-$C_{10}$-aryl or $C_5$-$C_{10}$-heteroaryl,
where the substituents are selected from the group consisting of $C_1$-$C_{15}$-alkyl, $C_1$-$C_6$-alkoxy, $C_5$-$C_{10}$-cycloalkyl and $C_5$-$C_{10}$-aryl;

$R^2$ and $R^3$ are each, independently of one another, hydrogen, unsubstituted or at least monosubstituted $C_1$-$C_{15}$-alkyl, $C_5$-$C_{10}$-cycloalkyl, $C_5$-$C_{10}$-heterocyclyl, $C_5$-$C_{10}$-aryl or $C_5$-$C_{10}$-heteroaryl,
  where the substituents are selected from the group consisting of $C_1$-$C_{15}$-alkyl, $C_5$-$C_{10}$-cycloalkyl and $C_5$-$C_{10}$-aryl
or
$R^2$ and $R^3$ together with the nitrogen atom form a five- or six-membered ring which optionally additionally comprises one or more heteroatoms selected from among O, S and N and bearing the substituent $R^4$, where
  $R^4$ is hydrogen or $C_1$-$C_6$-alkyl;
the process comprising:
reacting a reaction mixture (Rm) comprising carbon dioxide, hydrogen and an alcohol of the general formula (Ib)

$$R^1\text{—OH} \tag{Ib}$$

where $R^1$ has the above meanings,
or
an amine of the general formula (Ic)

$$NHR^2R^3 \tag{Ic}$$

where $R^2$ and $R^3$ each independently have the above meanings, in the presence of a catalyst comprising gold at a pressure in the range from 0.2 to 30 MPa and a temperature in the range from 20 to 200° C. in a hydrogenation reactor;
wherein the catalyst is a heterogeneous catalyst.

2. The process according to claim 1, wherein the catalyst comprises at least one support material.

3. The process according to claim 2, wherein the support material is selected from the group consisting of silicon dioxide, aluminum oxide, zirconium oxide, magnesium oxide and titanium oxide.

4. The process according to claim 2, wherein the heterogeneous catalyst comprises from 0.1 to 20% by weight of gold based on the total mass of the supported catalyst used.

5. The process according to claim 1, wherein an alcohol of the general formula (Ib) in which
  $R^1$ is unsubstituted or at least monosubstituted $C_1$-$C_8$-alkyl,
    where the substituents are selected from the group consisting of $C_1$-$C_6$-alkyl and $C_1$-$C_6$-alkoxy,
is used.

6. The process according to claim 5, wherein an alcohol selected from the group consisting of methanol, ethanol, 2-methoxyethanol, 1-propanol, 2-propanol, 1-butanol, 2-butanol, 2-methyl-1-propanol, 1-pentanol, 1-hexanol, 1-heptanol and 1-octanol is used as alcohol (Ib).

7. The process according to claim 5, wherein methanol is used as alcohol (Ib) and methyl formate is obtained as carboxylic acid derivative (Ia).

8. The process according to claim 1, wherein an amine selected from the group consisting of ammonia, methylamine, dimethylamine, ethylamine, diethylamine, n-propylamine, di-n-propylamine, isopropylamine, diisopropylamine, n-butylamine, di-n-butylamine, isobutylamine, diisobutylamine, morpholine, piperidine and piperazine is used as amine (Ic).

9. The process according to claim 8, wherein an amine selected from the group consisting of ammonia, methylamine and dimethylamine is used as amine (Ic).

10. The process according to claim 8, wherein ammonia is used as amine (Ic) and formamide is obtained as carboxylic acid derivative (Ia).

11. The process according to claim 1, wherein the residence time of the reaction mixture (Rm) in the hydrogenation reactor is from 10 minutes to 5 hours.

12. The process according to claim 11, wherein the mixture obtained in the reaction is worked up in a distillation apparatus to give
  a first stream comprising the carboxylic acid derivative (Ia),
  a second stream comprising unreacted alcohol (Ib) or unreacted amine (Ic) and
  a third stream comprising the water of reaction formed in the reaction.

13. The process according to claim 12, wherein the second stream is recirculated to the hydrogenation reactor.

* * * * *